United States Patent [19]
Jacobs et al.

[11] 3,989,698
[45] Nov. 2, 1976

[54] PROCESS FOR PREPARING BENZOXAZINES

[75] Inventors: Richard L. Jacobs, Perrysburg; Richard L. Hively, Toledo, both of Ohio

[73] Assignee: The Sherwin-Williams Company, Cleveland, Ohio

[22] Filed: Feb. 20, 1975

[21] Appl. No.: 551,803

[52] U.S. Cl. ............................................ 260/244 A
[51] Int. Cl.² .............. C07D 265/00; C07D 273/00; C07D 295/00
[58] Field of Search ......................... 260/244 A, 244

[56] References Cited
UNITED STATES PATENTS
3,531,509  9/1970  Sayigh et al. ........................ 260/244

OTHER PUBLICATIONS
Chem. Abst. 65 15371(d), (1966), Bolotin et al., "Synthesis and Optical . . . ."

*Primary Examiner*—Albert T. Meyers
*Assistant Examiner*—D. W. Robinson
*Attorney, Agent, or Firm*—James V. Tura; Richard G. Smith; Neil A. DuChez

[57] ABSTRACT

This invention relates to a process for preparing benzoxazines and more particularly 2-substituted-4H-3,1-benzoxazine-4-ones, obtained by reacting at least at about room temperature in the presence of an effective amount of a tertiary amine an isatoic anhydride with an acylating compound consisting of either a carboxylic acid anhydride or an acyl halide.

50 Claims, No Drawings

PROCESS FOR PREPARING BENZOXAZINES

SPECIFICATION

This invention is directed to benzoxazines and to a process for preparing benzoxazines and more particularly to a process for preparing 2-substituted-4H-3,1-benzoxazine-4-ones by reacting at temperatures of at least about 25° C in the presence of at least one tertiary amine, stoichiometric amounts of an isatoic anhydride with an acylating compound. The acylating compound may be either a carboxylic acid anhydride or an acyl halide, e.g. the chloride having up to 30 carbon atoms.

More specifically, this invention is directed to the preparation of substituted-4H-3,1-benzoxazines-4-ones wherein the substituent in the 2 position is either a saturated or unsaturated organic radical including the substituted and unsubstituted organic radicals selected from the class consisting of the alkyl, aryl, alkaryl, aralkyl, cycloalkyl and various heterocyclic radicals. The isatoic anhydride includes the substituted anhydrides which are reacted in stoichiometric amounts with the acylating compound, e.g. acyl halide or carboxylic acid anhydride to obtain either substituted benzoxazines, bis-benzoxazines or dibenzoxazines depending upon the particular acylating compound.

The 2-substituted benzoxazines of this invention may be used for a variety of purposes including, for example, fungicides, insecticides or herbicides, and particularly as intermediates in the synthesis of various pharmacological compounds such as the quinazolinones, e.g. the substituted-4-(3H)-quinazolinones which are known to possess anticonvulsant and sedative properties.

BACKGROUND

The 4H-3,1-benzoxazine-4-ones and the various derivatives thereof are known in the art. These benzoxazines generally are prepared, for example, by reacting a mole of anthranilic acid with a substantial excess, i.e. two moles or more of an acylating compound, e.g. an aryloyl chloride in order to produce high yields of 2-aryl-4H-3,1-benzoxazine-4-ones. However, when an excessive amount of the acylating compound is used, i.e. one mole in excess of the stoichiometric amount needed to obtain the benzoxazines, they are contaminated with the corresponding carboxylic acid which is difficult to separate from the product.

Attempts to avoid this problem by decreasing the acylating compound to a stoichiometric amount of about one mole, resulted in yields of benzoxazine of only 30 to 40%. In theory, this low yield is believed to be due to an initial competitive reaction, i.e. the initial acylation of anthranilic acid resulting in a reaction mixture containing intermediates only one of which continues to react to form the benzoxazine while the other needs the addition of a second mole of acylating compound in order to form the benzoxazine in desired yields. In other words, in a 1:1 mole ratio reaction of the anthranilic acid with the acylating compound, less than about 1/2 of the acylating compound is converted to benzoxazine with the remaining being converted to carboxylic acid. To illustrate that only about 1/2 of the acylating compound is converted to benzoxazine, the anthranilic acid was reacted first with one mole of o-nitrobenzoyl chloride followed by reacting that mixture with a mole of benzoyl chloride. The only product obtained from that reaction was 2-(o-nitrophenyl)-4H-3,1-benzoxazine-4-one. This shows that when one mole of anthranilic acid is reacted with one mole of acylating compound only one of the intermediates initially formed is converted to the benzoxazine, i.e. nitrophenyl-substituted benzoxazine. Therefore, since it was recognized that the organic groups, e.g. aryl groups of these acylating compounds do not mix as illustrated by the nitrobenzoyl chloride reaction, it was prudent in preparing benzoxazines first to react the anthranilic acid with the more expensive acylating compound, e.g. the acyl chloride in a 1:1 ratio to insure that all of said acylating compound is converted and then to complete the reaction with the addition of a less expensive acylating compound such as acetic anhydride.

SUMMARY

In accordance with this invention, it has been found that the 2-substituted-4H-3,1-benzoxazine-4-ones can be prepared by reacting approximately stoichiometric amounts of an isatoic anhydride with an acylating compound, i.e. either a carboxylic acid anhydride or the halide thereof in the presence of a tertiary amine such as pyridine, to obtain benzoxazines in high yields without the presence of large amounts of contaminants such as carboxylic acid. In accordance with this invention, only stoichiometric amounts of the reactants are necessary with a comparatively small excess over the theoretical amount needed to obtain benzoxazines. Substantially pure products may be recovered, e.g. by crystallization, etc. from the reaction mixture or it may be used directly for reaction with other reagents, e.g. hydroxylamine-hydrochloride, amines, alcohols, water etc. to form other products such as the quinazolinones or the corresponding anthranilic acids in high yields.

Accordingly, it is an object of this invention to provide a process for preparing benzoxazines and more particularly 2-substituted benzoxazines in high yields from stoichiometric amounts of isatoic anhydride and an acylating compound. It is another object of this invention to provide a process for preparing 2-substituted-4H-3,1-benzoxazine-4-ones in high yields wherein the reaction mixture can be used without prior separation of the product for reaction with other reagents to obtain various other useful compounds. It is still another object of this invention to provide a process whereby 2-substituted benzoxazines can be obtained free of contaminants by reacting substantially stoichiometric amounts of an isatoic anhydride with an acylating compound.

These and other objects will become apparent from a further and more detailed description of the invention as follows.

DETAILED DESCRIPTION

This invention related to a process for preparing benzoxazines and more particularly the 2-substituted-4H-3,1-benzoxazine-4-ones by reacting at a temperature of at least about 25° C and in the presence of an effective amount of at least one tertiary amine, a stoichiometric amount of an isatoic anhydride with an acylating compound selected from the class consisting of (a) carboxylic acid anhydrides having up to 30 carbon atoms and at least one anhydride group per molecule, i.e.

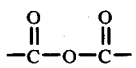

and (b) acyl halides having the formula

 I.

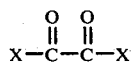 II.

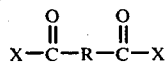 III.

wherein X is a halogen, e.g. chlorine, bromine, iodine or fluorine and R is a saturated or unsaturated organic radical having up to 30 carbon atoms. More specifically, R may be either a substituted or unsubstituted organic radical selected from the class consisting of alkyl, aryl, alkaryl, aralkyl, cycloalkyl and heterocyclic radicals. These organic radicals may be substituted with one or more non-reactive substituents including, for example, substituents preferably selected from the class consisting of halo such as chloro, bromo, etc., nitro, carbon trichloride, lower dialkylamino, diarylamino, lower trihaloalkyl such as trifluoromethyl, trifluoroethyl, etc., lower carboalkoxy such as carbomethoxy, carboethoxy, etc., lower alkoxy such as methoxy, aroxy such as phenoxy and various other substituents which do not interfer with the reaction of the isatoic anhydride with the acylating compound. The term lower, for purposes of this invention, includes organic radicals having from 1 to 8 carbon atoms.

The isatoic anhydride also may be a substituted anhydride having from 0 to 4 substituents on the ring characterized by the formula

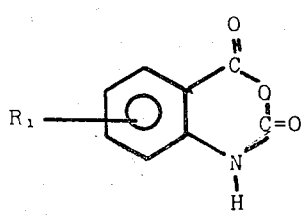

wherein $R_1$, for example, may include various non-reactive substituents as recited hereinabove and preferably substituents selected from the class consisting of hydrogen, halo, nitro, lower alkoxy, lower alkenyloxy or lower alkyl radical of 1 to 8 carbon atoms.

The isatoic anhydride is reacted with the acylating compound, e.g. carboxylic acid anhydride or acyl halide in approximately stoichiometric amounts with only a comparatively small excess, e.g. excess amounts which may range up to about 30% and preferably only up to 10% excess over the theoretical amount required for the reaction. Generally, the stoichiometric amount for purposes of this invention is approximately a 1 to 1 molar ratio of the isatoic anhydride to the acyl compound, e.g.

or

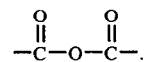.

However, where the acyl compound has more than one functional group, i.e. is an acyl dihalide then the acylating compound is used in amounts of approximately one mole of the acylating compound, e.g.

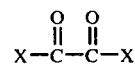

for every two moles of the isatoic anhydride. Specifically, for example, in the preparation of either a di- or bis-2-substituted-4H-3,1-benzoxazine-4-one, approximately 1/2 mole of the acyl dihalide, e.g.

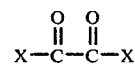

or

will be needed for every mole of isatoic anhydride. The reaction generally takes place at temperatures as low as room temperature or from about 25° C ranging up to about 150° C and preferably at temperatures ranging from about 80° C to 120° C in the presence of at least one tertiary amine.

AMINES

The tertiary amines, for purposes of this invention, may be used in small, but effective amounts, i.e. catalytic amounts of less than about 0.1 times by weight of the amount of isatoic anhydride and in larger amounts ranging, for example, up to about 20 times or more of the amount by weight of the isatoic anhydride and preferably in an amount ranging from about 1.0 to 10 times by weight of the isatoic anhydride present in the reaction mixture.

The amines are tertiary amines such as the aliphatic, aromatic and cyclic tertiary amines having up to 20 carbon atoms and the various substituted aliphatic, aromatic or cyclic amines. Of the various tertiary amines, the preferred are the pyridines and quinolines such as, for example, benzyl pyridine, butyl pyridine, phenyl pyridine, propyl pyridine, methoxy pyridine, trimethyl quinoline, phenyl quinoline, methyl quinoline, benzyl quinoline, methoxyquinoline and various combinations thereof in any proportion. In addition to pyridine, the homologs of pyridine may be used which includes the methyl pyridines or picolines, dimethyl pyridine, ethyl pyridine, trimethyl pyridine, 5-ethyl-2-methyl pyridine, diethyldimethyl pyridine etc. Various other tertiary amines that may be used include, for example, dimethylethyl amine, triphenyl amine, methyldiethyl amine, tripropyl amine, trimethyl amine, triethyl amine, triamyl amine, tributyl amine and various other aliphatic or cycloaliphatic tertiary amines. An illustration of some other amines that may be used include the dialkyl toluidines such as dimethyl toluidine, the N,N-dialkylanilines such as N,N-dimethyl aniline, N,N-diethyl aniline, etc., the N-substituted alkyl pyrrolines such as methyl pyrroline, ethyl pyrroline, etc., the N-substituted alkyl pyrroles such as methyl pyrrole, ethyl pyrrole, etc., the N-substituted alkyl piperidines, the N-substituted alkyl piperazines and various other tertiary amines and combinations thereof in any proportion.

ANHYDRIDE ACYLATING COMPOUNDS

The carboxylic acid anhydrides include the saturated or unsaturated aliphatic, cycloaliphatic or aromatic anhydrides. These anhydrides, i.e.

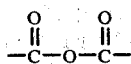

may have substituted or unsubstituted mono- or divalent organic radicals with up to 30 carbon atoms. More specifically, the carboxylic acid anhydrides may be characterized by the formula which has either one divalent or two monovalent R groups

wherein R is an organic radical or substituted organic radical, saturated or unsaturated, selected from the class consisting of alkyl, aryl, alkaryl, aralkyl, cycloalkyl, and heterocyclic radicals. Again, these organic radicals may have one or more non-reactive substituents including the substituents particularly recited hereinabove in illustrating the substituents on the organic radicals of the acyl halides.

More specifically, the carboxylic acid anhydrides include the saturated acid anhydrides such as acetic, propionic and butyric anhydride, etc. The unsaturated acid anhydrides include acrylic, substituted acrylic, crotonic and oleic anhydride, etc. The aromatic carboxylic acid anhydrides include, for example, phenylacetic anhydride, phthalic anhydride, and benzoyl phthalic anhydride, etc. An illustration of other anhydrides include chloroacetic anhydride, caproic anhydride, caprylic anhydride, palmitic anhydride, phenoxyacetic anhydride, lauric anhydride, heptylic anhydride, myristic anhydride, stearic anhydride, sulfobenzoic anhydride, valeric anhydride, benzoic anhydride, benzoyl acetic anhydride, nitrophthalic anhydride, tetrahydrophthalic anhydride, cinnamic anhydride, 2-nitro-cinnamic anhydride, naphthenic anhydride, 3-cyclohexene-1,2-dicarboxylic anhydride, etc.

As illustrated above, the acyl halides may be characterized by having one or more acyl groups, i.e.

where X is halogen and includes, for example, the acyl mono- and dihalides, i.e. chlorides, bromides, iodides and fluorides, such as the benzoyl halides, i.e. benzoyl chloride, benzoyl bromide, benzoyl fluoride, benzoyl iodide, the acetyl halides such as acetyl chloride, acetyl bromide, acetyl iodide, acetyl fluoride and various bromoacetyl haloacetyl chlorides such as bromoacetyl chloride, chloroacetyl chloride, etc. Other acyl halides include halobenzoyl halides such as chlorobenzoyl chloride, bromobenzoyl chloride and various substituted benzoyl halides such as nitrobenzoyl chloride or bromide, etc. In addition, other acyl halides include myristyl chloride, palmityl chloride, pelargonyl chloride, phenylacetyl chloride, propionyl chloride, butyryl chloride, capryl chloride, lauryl chloride, crotonyl chloride, valeryl chloride, naphthyl chloride, stearyl chloride and the dihalides such as succinyl dichloride or dibromide, phthalyl dichloride, isophthalyl dichloride, terephthalyl dichloride, oxalyl dichloride or dibromide, pivaloyl dichloride, cinnamoyl chloride, etc. As an example, these carboxylic acid halides may be prepared by reacting the acid or its anhydride by known methods with a halogenating agent such as phosphorous trichloride or tribromide, phosphorous pentachloride, thionyl chloride, etc.

The isatoic anhydrides are reacted with the acyl compounds in the presence of an effective amount of at least one tertiary amine preferably pyridine and in an amount sufficient that the amine functions not only as a catalyst, but also as a solvent depending upon the reactants and may be used either alone or in combination with various other known non-reactive organic liquids. Specifically, the other organic liquids which may be used in combination with the tertiary amine include, for example, dioxane, the nitriles such as benzonitrile, and various other aromatic or aliphatic solvents such as benzene, xylene, toluene, cyclohexane, the ketones such as methyl ethyl ketone, acetone, the acetates such as methyl acetate, the glycol ethers such as diethoxy ethane, the aliphatic solvents such as hexane, octane, pentane and various combinations thereof in any proportion.

The following examples illustrate the process for preparing benzoxazines for purposes of this invention and particularly their use as intermediates in the production of other useful compositions.

EXAMPLE 1

| Reagents | Parts by Weight |
| --- | --- |
| Isatoic Anhydride | 50 (0.306 mole) |
| Acetic Anhydride | 50 (0.49 mole) |
| Pyridine | 150 ml |

The isatoic anhydride and pyridine were combined in a round bottomed, 3-necked flask equipped with a mechanical stirrer, thermometer, reflux condenser, dropping funnel and drying tube. The isatoic anhydride suspension was heated to 45° C and the acetic anhydride was added over a period of 30 minutes. Carbon dioxide evolution occurred during the addition of the acetic anhydride. The reaction mixture was heated to 90° C for 1.5 hours. The evolution of carbon dioxide stopped. The reaction mixture was concentrated under reduced pressure (15 mm. of Hg). The residue was crystallized from 100 ml of cyclohexane to give 42 parts by weight (86% yield) of 2-methyl-4H-3,1-benzoxazine-4-one with m.p. 79°–81° C.

EXAMPLE 2

| Reagents | Parts by Weight |
| --- | --- |
| Isatoic Anhydride | 50 (0.306 mole) |
| Acetic Anhydride | 40 (0.39 mole) |
| Pyridine | 100 ml |

The reaction was run as described above. The pyridine and acetic acid formed in the reaction were removed by distillation at 80° C and 20 min. of Hg. The resulting residue was distilled under reduced pressure to give 44.2 parts by weight (88.8% yield) of 2-methyl-4H-3,1-benzoxazine-4-one with b.p. 95°–100° C at 3 mm. of Hg. The NMR (nuclear magnetic resonance) spectrum of the product showed the material to be pure.

EXAMPLE 3

Two experiments were run in order to determine if the 2-methyl-4H-3,1-benzoxazine-4-one could be prepared in solvents other than pyridine. In these experiments only a small excess of pyridine was used.

| Reagents | Parts by Weight |
| --- | --- |
| Isatoic Anhydride | 50 (0.306 mole) |
| Acetic Anhydride | 40 (0.39 mole) |
| Pyridine | 31.6 (0.40 mole) |
| Acetic Acid | 100 ml |

The above reagents were combined and heated to reflux for 2 hours. The solvent was distilled from the reaction mixture under reduced pressure (20 mm. of Hg) to give 53.5 parts of solid residue. Care was taken to trap the recovered mixture of pyridine and acetic acid. The residue from the distillation was analyzed by NMR. The analysis showed the crude reaction product consisted of 89.5% of 2-methyl-4H-3,1-benzoxazine-4-one. The data showed that 97.1% of the isatoic anhydride charged in the reaction was converted to the benzoxazine.

EXAMPLE 4

| Reagents | Parts by Weight |
| --- | --- |
| Isatoic Anhydride | 50 (0.306 mole) |
| Acetic Anhydride | 40 (0.39 mole) |
| Solvent | The solvent recovered from Example 3 was used. |

The above reagents were reacted in the same manner as described in Example 3. About 57 parts by weight of crude reaction product was obtained which contained 84.5% of 2-methyl-4H-3,1-benzoxazine-4-one. The data showed that 97.8% of the isatoic anhydride charged was converted to the benzoxazine.

EXAMPLE 5

| Reagents | Parts by Weight |
| --- | --- |
| Isatoic Anhydride | 16.3 (0.1 mole) |
| Pivaloyl Chloride | 13.2 (0.11 mole) |
| Pyridine | 100 ml |

The isatoic anhydride and pyridine were placed in a round bottomed, three neck flask equipped with a mechanical stirrer, reflux condenser, thermometer and drying tube. The pyridine solution was heated to 50° C and the pivaloyl chloride was added over a period of 30 minutes. The reaction mixture was heated to 100°–105° C for 8 hours and then the product was extracted from precipitated pyridine hydrochloride with benzene and allowed to stand at room temperature.

The solid that precipitated on standing was isolated and identified as pyridine hydrochloride. The filtered pyridine reaction mixture was concentrated under reduced pressure. The resulting residue was extracted with 200 ml of hot benzene. The benzene extract was cooled to room temperature. The small amount of solid that formed was removed by filtration. This solid was pyridine hydrochloride. The benzene solution was concentrated under reduced pressure. The resulting residue was crystallized from 50 ml of petroleum ether (30°–60° C) to give 12 parts by weight (59% yield) of 2-tertiary-butyl-4H-3,1-benzoxazine-4-one.

PRODUCT CHEMICAL ANALYSIS

| | $C_{12}H_{13}NO_2$ | |
| --- | --- | --- |
| | Calculated | Found |
| Carbon | 70.91 | 70.91 |
| Hydrogen | 6.45 | 6.45 |
| Nitrogen | 6.89 | 6.91 |

EXAMPLE 6

| Reagents | Parts by Weight |
| --- | --- |
| Isatoic Anhydride | 16.3 (0.1 mole) |
| Cinnamoyl Chloride | 16.7 (0.1 mole) |
| Pyridine | 100 ml |

The isatoic anhydride and pyridine were placed in a three-necked, round-bottomed flask equipped with a mechanical stirrer, reflux condenser, dropping funnel, thermometer and drying tube. The pyridine suspension of isatoic anhydride was warmed to 40° C until all of the isatoic anhydride was in solution. The pyridine solution was allowed to cool to room temperature. The cinnamoyl chloride dissolved in 50 parts of toluene was added to the isatoic anhydride solution over a period of 20 minutes. After all the cinnamoyl chloride was added, the reaction mixture was refluxed for 15 minutes. The reaction mixture was cooled in an ice bath for 30 minutes. The resulting solid was isolated and washed with 200 parts of cold water containing 10 parts of concentrated hydrochloric acid. This solid was air dried. The dried solid was crystallized from 150 parts of benzene to give a solid material. This solid was washed with water, dried and crystallized from benzene to give an additional 3.6 parts by weight of the 2-styryl-4H-3,1-benzoxazine-4-one having mp 145°–147° C. The total yield was 23.2 parts (93% yield).

PRODUCT CHEMICAL ANALYSIS

| | $C_{16}H_{11}NO_2$ | |
| --- | --- | --- |
| | Calculated | Found |
| Carbon | 77.66 | 77.2 |
| Hydrogen | 4.45 | 4.9 |

-continued

|  | $C_{16}H_{11}NO_2$ | |
|---|---|---|
|  | Calculated | Found |
| Nitrogen | 5.62 | 5.3 |

EXAMPLE 7

| Reagents | Parts by Weight |
|---|---|
| Isatoic Anhydride | 32.6 (0.2 mole) |
| Benzoyl Chloride | 32.3 (0.23 mole) |
| Pyridine | 150 ml |

The isatoic anhydride and pyridine were combined in a three-necked, round-bottomed flask equipped with a dropping funnel, thermometer, mechanical stirrer and drying tube. A pyridine suspension of isatoic anhydride was heated to 40° C and the addition of the benzoyl chloride was started. The benzoyl chloride was added over a period of 20 minutes. The reaction mixture was refluxed for 2 hours. Most of the pyridine was removed by distillation under reduced pressure. The resulting residue was treated with 200 ml of cold water containing 10 ml of concentrated hydrochloric acid. The resulting solid was isolated by filtration. The filter cake was washed with 200 parts of cold H₂O. The isolated solid was dried at 100° C for 18 hours. The yield of 2-phenyl-4H-3,1-benzoxazine-4-one was 40 parts (89.7% yield) with m.p. 117°–119° C.

PRODUCT CHEMICAL ANALYSIS

|  | $C_{14}H_9NO_2$ | |
|---|---|---|
|  | Calculated | Found |
| Carbon | 75.30 | 75.40 |
| Hydrogen | 4.06 | 4.10 |
| Nitrogen | 6.28 | 6.26 |

In the following table, 2-Substituted-4H-3,1-benzoxazine-4-ones were prepared by the reaction of an isatoic anhydride with a carboxylic acid anhydride or chloride thereof in the presence of pyridine. The following equations illustrate the reaction of the isatoic anhydrides with the various acylating compounds.

I. 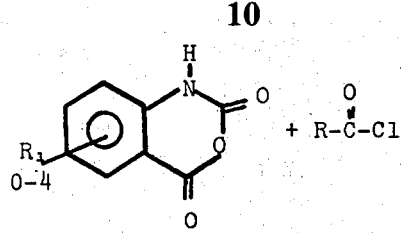

Isatoic Anhydride + Acylating Compound

II. 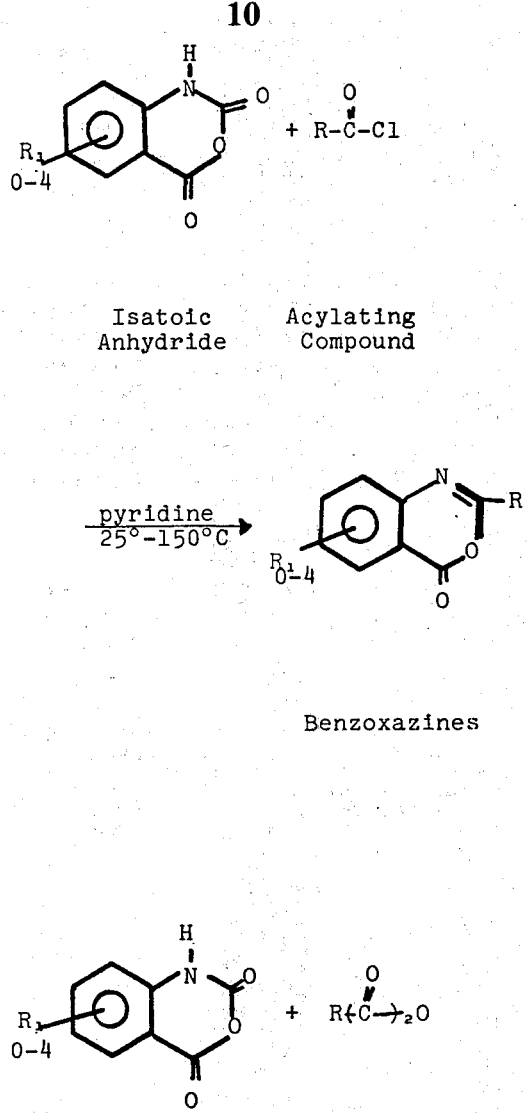

Benzoxazines

TABLE I

| Examples | Substituents 0 to 4 $R_1$ | R Substituted or Unsubstituted Organic Radical | % Yield by Weight Benzoxazines | M.P.° C of | Moles of Carboxylic Acid Chloride or Anhydride | Moles of Isatoic Anhydride or Substituted Isatoic Anhydride |
|---|---|---|---|---|---|---|
| 8 | H | CH₃—(methyl) | 89 | 79–81 | 0.3 | 0.3 |
| 9 | H | CH₃—(CH₂)₁₄—(pentadecyl) | 73 | 65–68 | 0.11 | 0.10 |
| 10 | H | CH₃—C(CH₃)(CH₂)—(t-butyl) | 59 | 71–73 | 0.11 | 0.10 |
| 11 | H | C₆H₅—CH=CH—(styryl) | 93 | 145–147 | 0.10 | 0.10 |

TABLE I-continued

| Examples | Substituents 0 to 4 $R_1$ | R Substituted or Unsubstituted Organic Radical | % Yield by Weight of Benzoxazines | M.P.° C of | Moles of Carboxylic Acid Chloride or Anhydride | Moles of Isatoic Anhydride or Substituted Isatoic Anhydride |
|---|---|---|---|---|---|---|
| 12 | H | (phenyl) | 90 | 117–119 | 0.23 | 0.20 |
| 13 | H | (o-chlorophenyl) | 81 | 138–139 | 0.11 | 0.10 |
| 14 | H | (p-chlorophenyl) | 88 | 188–189 | 0.11 | 0.10 |
| 15 | H | (o-methoxyphenyl) | 91 | 127–128 | 0.11 | 0.10 |
| 16 | H | (p-methoxyphenyl) | 85 | 150–151 | 0.11 | 0.10 |
| 17 | H | (m-nitrophenyl) | 88 | 167–168 | 0.11 | 0.10 |
| 18 | H | (p-nitrophenyl) | 99 | 202–203 | 0.105 | 0.10 |
| 19 | H | (2-furfuryl) | 88 | 105–106 | 0.11 | 0.10 |
| 20 | H | $CCl_3$—(trichloromethyl) | 59 | 94–95 | 0.105 | 0.10 |
| 21 | Cl | $CH_3$—methyl | 72 | 122–124 | 0.105 | 0.10 |
| 22 | $NO_2$ | $CH_3$—methyl | 55 | 153–155 | 0.105 | 0.11 |
| 23 | H | Bis-4H-3,1-benzoxazine-4-one | 86 | >300 | 0.05 | 0.10 |
| 24 | H | 2,2'-p-phenylene di-4H-3,1-benzoxazine-4-one | 81 | >300 | 0.30 | 0.60 |

*Product of Example 23 was derived from oxalyl chloride, i.e.

$$(Cl-\overset{O}{\underset{\|}{C}}-\overset{O}{\underset{\|}{C}}-Cl).$$

Product of Example 24 was derived from terephthalyl chloride, i.e. $C_6H_4$—$(COCl)_2$.

EXAMPLE 23 (Shown in Table I)

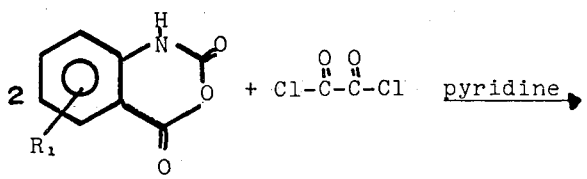

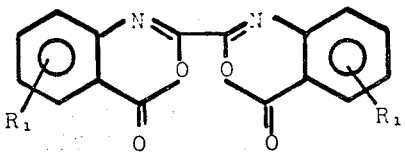

| Reagents | Parts by Weight |
|---|---|
| Isatoic Anhydride | 16.3 (0.1 mole) |
| Oxalyl Chloride | 6.3 (0.05 mole) |
| Pyridine | 75 ml |

The isatoic anhydride and pyridine were placed in a three necked, round bottomed flask equipped with a mechanical stirrer, dropping funnel, reflux condenser, thermometer and drying tube. The oxalyl chloride dissolved in 50 ml of toluene was added to the isatoic anhydride pyridine suspension over a period of 30 minutes. The reaction mixture was heated to reflux for 90 minutes and cooled to room temperature. The solid that was formed was isolated and washed by suspending in 200 ml of cold water. The solid was separated from the water by filtration and dried at room temperature in a vacuum desiccator over night. The yield of bis-4H-3,1-benzoxazine-4-one was 12 parts (86% yield) with m.p. >300° C.

EXAMPLE 24 (Shown in Table I)

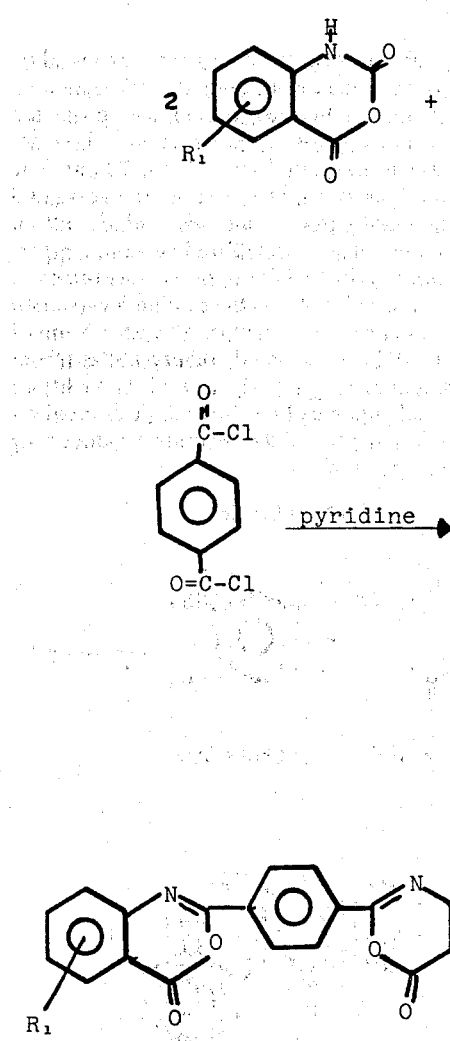

2,2'-p-phenylene-di-4H-3,1-Benzoxazine-4-one

| Reagents | Parts by Weight |
|---|---|
| Isatoic Anhydride | 97.4 (0.60 mole) |
| Terephthalyl Chloride | 60.99 (0.30 mole) |
| Pyridine (dry) | 1000 ml |

The isatoic anhydride and pyridine is added to a 2 l., three necked, round bottomed flask equipped with a mechanical stirrer, reflux condenser, drying tube and thermometer. The pyridine suspension was heated to 60° C at which point all of the isatoic anhydride dissolved. The solid terephthalyl chloride was added to the reaction mixture over a period of 15 minutes. Rapid gas evolution was noted, after about ¼ of the chloride was added. After all of the terephthalyl chloride was added, the reaction mixture was heated to reflux for four hours. The reaction mixture was cooled to room temperature. The solid that had formed during the course of the reaction was isolated. The solid was suspended in 300 ml of cold water and isolated by filtration. The filter cake was washed with 200 ml of methanol and then 200 ml of acetone. The solid was dried at 100° C for 18 hours to give 92 parts (81% yield) of the 2,2'-p-phenylene-di-4H-3,1-benzoxazine-4-one with m.p. >300° C.

The reaction mixtures which contain the benzoxazines as prepared in accordance with this invention may be used directly without separation or purification in the preparation of various other related compounds and particularly in the preparation of the corresponding anthranilic acids and the esters thereof as particularly illustrated by Examples 25 and 26.

EXAMPLE 25

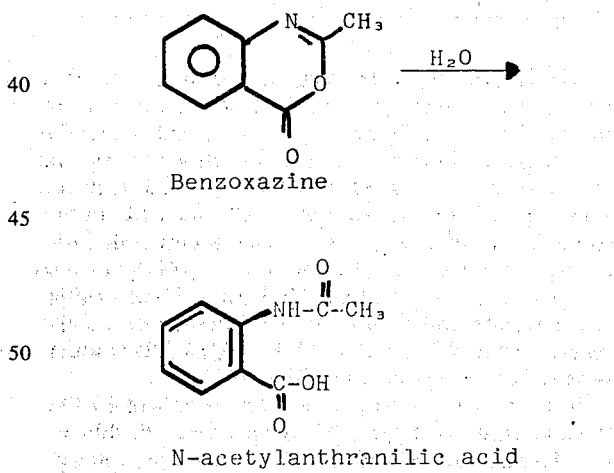

| Reagents | Parts by Weight |
|---|---|
| Isatoic Anhydride | 50 (0.306 mole) |
| Acetic Anhydride | 50 (0.49 mole) |
| Pyridine | 150 ml |

The isatoic anhydride and acetic anhydride were combined in a three necked, round bottomed flask equipped with a mechanical stirrer, dropping funnel, thermometer, reflux condenser and drying tube. The acetic anhydride was added to the mixture through the dropping funnel over a period of 30 minutes. The reaction was heated to 90°–100° C for 1.5 hours and then cooled to room temperature. The cooled reaction mixture was poured into a kilogram of ice containing 150 ml of concentrated hydrochloric acid. The white solid which precipitated was isolated, washed with 200 ml of water and dried to give 51.5 parts (94% yield) of N-acetylanthranilic acid having m.p. 183°–185° C.

EXAMPLE 26

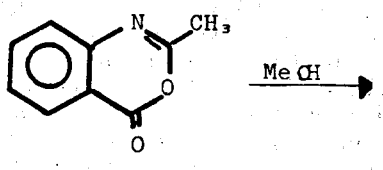

Benzoxazine

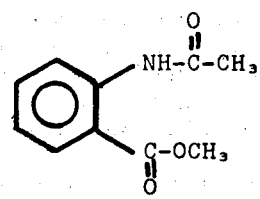

Methyl N-Acetylanthranilate

| Reagents | Parts by Weight |
|---|---|
| Isatoic Anhydride | 10 (0.060 mole) |
| Acetic Anhydride | 7.0 (0.070 mole) |
| Triethyl Amine | 50 ml |
| Methanol | 50 ml |

The isatoic anhydride, acetic anhydride and triethylamine were combined in a three necked, round bottomed flask equipped with a mechanical stirrer, reflux condenser and drying tube. The reaction mixture was refluxed for 2 hours. The methanol was added to the mixture, refluxed for an additional hour and concentrated under reduced pressure. The resulting solid residue was treated with 200 ml of water. The solid was isolated and dried. NMR analysis showed that methyl N-acetylanthranilate was formed and was essentially pure. About 10.5 parts (90.5% yield) of the product was isolated which had m.p. 96°–98° C.

Similarly, the reaction mixture which contain the benzoxazines as prepared in accordance with this invention may be used without first separating or purifying in the preparation of quinazolinones as illustrated by Examples 27, 28 and 29.

EXAMPLE 27

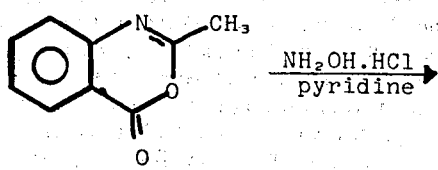

| Reagents | Parts by Weight |
|---|---|
| Isatoic Anhydride | 10 (0.06 mole) |
| Acetic Anhydride | 7.0 (0.07 mole) |
| Hydroxylamine-hydrochloride | 10.4 (0.15 mole) |
| Pyridine | 50 ml |

The isatoic anhydride, acetic anhydride and pyridine were combined in a round bottomed flask equipped with a thermometer, reflux condenser and protected from atmospheric moisture by a drying tube. The reaction mixture was heated to 90°–100° C for 1 hour. The reaction mixture was cooled to room temperature and the hydroxylamine-hydrochloride was added all at once. The reaction mixture was stirred at room temperature for 24 hours. Most of the pyridine was removed from the reaction product by distillation under reduced pressure. The solid residue was slurried with 150 ml of cold water. The solid was isolated and crystallized from 200 ml of methanol to give 7.4 parts (70% yield) of 4-hydroxy-2-methylquinazoline-3-oxide. It is obvious from the above that part of the reaction product may exist in the tautomeric form.

EXAMPLE 28

Benzoxazine    Toluidine

| Reagents | Parts by Weight |
|---|---|
| Isatoic Anhydride | 16.3 (0.10 mole) |
| Acetic Anhydride | 11.0 (0.11 mole) |
| Pyridine | 50 ml |
| o-Toluidine | 13.0 (0.13 mole) |

The isatoic anhydride and acetic anhydride were reacted under the condition described for the preparation of 2-methyl-4H-3,1-benzoxazine-4-one. The pyridine was distilled from the reaction mixture under reduced pressure. The crude reaction product was taken up in 100 ml of o-xylene and placed in a 200 ml one-necked flask equipped with a Dean-Stark trap and a reflux condenser. The o-toluidine was added to the xylene solution. The reaction mixture was heated to reflux for 4 hours. 1.8 ml of water was collected in the Dean-Stark trap. The xylene was removed from the reaction product by distillation under reduced pressure. The resulting residue was crystallized twice from methanol to give 16 parts (64% yield) of 2-methyl-3-(o-tolyl)-quinazoline-4 (3H)-one with m.p. 113°–115° C. The reaction product was characterized by melting point, IR and NMR.

EXAMPLE 29

| Reagents | Parts by Weight |
| --- | --- |
| Isatoic Anhydride | 8.2 (0.05 mole) |
| Acetic Anhydride | 5.5 (0.055 mole) |
| o-Toluidine | 7.0 (0.065 mole) |
| Pyridine | 25 ml |

The reaction of isatoic anhydride with acetic anhydride in pyridine was carried out in the manner described for the preparation of 2-methyl-4H-3,1-benzoxazine-4-one. The reaction mixture was cooled to room temperature and the o-toluidine added all at once. The reaction mixture was stirred at room temperature for 16 hours. The solvent was distilled off under reduced pressure. The residue, 11.5 parts was analyzed by NMR. The NMR spectrum showed that 95% of the crude reaction product was 2-methyl-3-(o-tolyl)-quinazoline-4-one. The crude reaction product was crystallized from 25 ml of methanol to give 9.7 parts (78% yield) of 2-methyl-3-(o-tolyl)-quinazoline-4-one with m.p. 113°–115° C.

PRODUCT CHEMICAL ANALYSIS

| | $C_{16}H_{14}N_2O$ | |
| --- | --- | --- |
| | Calculated | Found |
| Carbon | 76.77 | 76.74 |
| Hydrogen | 5.64 | 5.76 |
| Nitrogen | 11.20 | 11.16 |

While this invention has been described by a number of specific embodiments, it is obvious there are variations and modifications which can be made without departing from the spirit and scope of the invention as set forth in the appended claims.

The invention claimed is:

1. A process for preparing benzoxazines which comprises reacting at temperatures of at least about 25° C in the presence of a catalytic amount of at least one tertiary amine, approximately stoichiometric amounts of an isatoic anhydride with an acylating compound selected from the class consisting of (a) carboxylic acid anhydrides and (b) acyl halides having the formulae

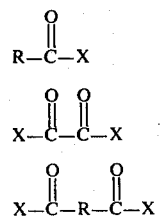

wherein X is halogen and R is a saturated or unsaturated organic radical having up to 30 carbon atoms.

2. The process of claim 1 further characterized in that R is a substituted or unsubstituted organic radical selected from the class consisting of alkyl, aryl, alkaryl, aralkyl, cycloalkyl, and heterocyclic radicals.

3. The process of claim 2 further characterized in that R is a substituted-organic radical.

4. The process of claim 1 further characterized in that the benzoxazine is 2-alkyl-4H-3,1-benzoxazine-4-one prepared by reacting the isatoic anhydride with an aliphatic carboxylic acid anhydride having up to 30 carbon atoms.

5. The process of claim 1 further characterized in that the benzoxazine is 2-alkyl-4H-3,1-benzoxazine-4-one prepared by reacting the isatoic anhydride with an aliphatic acyl chloride.

6. The process of claim 1 further characterized in that the benzoxazine is 2-aryl-4H-3,1-benzoxazine-4-one prepared by reacting the isatoic anhydride with an aromatic carboxylic acid anhydride having up to 30 carbon atoms.

7. The process of claim 1 further characterized in that the benzoxazine is 2-substituted-aryl-4H-3,1-benzoxazine-4-one prepared by reacting the isatoic anhydride with an aromatic acyl chloride.

8. The process of claim 1 further characterized in that the halogen is chlorine.

9. The process of claim 1 further characterized in that the tertiary amine comprises pyridine and is present in an amount ranging up to about ten times the amount by weight of the isatoic anhydride.

10. The process of claim 1 further characterized in that the reaction temperature ranges from about 25° C to about 125° C.

11. The process of claim 1 further characterized in that the isatoic anhydride is a substituted-isatoic anhydride having 0 to 4 substituents.

12. The process of claim 11 further characterized in that the substituted-isatoic anhydride has the formula

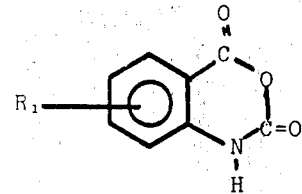

wherein $R_1$ is selected from the class consisting of hydrogen, halo, nitro, lower alkoxy, alkenyloxy or alkyl radical of 1 to 8 carbon atoms.

13. The process of claim 1 further characterized in that a 4H-3,1-benzoxazine-4-one is prepared by reacting about 1.0 mole of an isatoic anhydride with about 1.0 mole of a saturated or unsaturated carboxylic acid anhydride.

14. The process of claim 13 further characterized in that the carboxylic acid anhydride is an aliphatic carboxylic acid monoanhydride.

15. The process of claim 13 further characterized in that the carboxylic acid anhydride is an aromatic carboxylic acid monoanhydride.

16. The process of claim 14 further characterized in that the monoanhydride is acetic acid anhydride.

17. The process of claim 15 further characterized in that the aromatic carboxylic acid monoanhydride is a substituted-aromatic monoanhydride.

18. The process of claim 14 further characterized in that the carboxylic acid anhydride is a substituted-aliphatic carboxylic acid monoanhydride.

19. The process of claim 1 further characterized in that a di-4H-3,1-benzoxazine-4-one is prepared by reacting about 1.0 mole of an isatoic anhydride with about 1.0 mole of carboxylic acid anhydride in the presence of effective amounts of pyridine.

20. The process of claim 19 further characterized in that the carboxylic acid anhydride is acetic anhydride.

21. The process of claim 19 further characterized in that the carboxylic acid anhydride is a substituted-aromatic carboxylic acid anhydride.

22. The process of claim 13 further characterized in that the carboxylic acid anhydride has the formula

wherein R is either a divalent or monovalent organic radical having up to 30 carbon atoms and is selected from the class consisting of alkyl, aryl, alkaryl, aralkyl, cycloalkyl and heterocyclic radicals.

23. The process of claim 22 further characterized in that R is styryl radical.

24. The process of claim 22 further characterized in that R is phenyl radical.

25. The process of claim 22 further characterized in that R is a halo-substituted phenyl radical.

26. The process of claim 22 further characterized in that R is an alkoxy-substituted phenyl radical.

27. The process of claim 22 further characterized in that R is nitro-substituted phenyl radical.

28. The process of claim 22 further characterized in that R is a halo-substituted alkyl radical.

29. The process of claim 28 further characterized in that the halo-substituted alkyl radical is chloromethyl.

30. The process of claim 25 further characterized in that the halo-substituted phenyl radical is chloro-substituted phenyl radical.

31. The process of claim 26 further characterized in that the alkoxy-substituted phenyl radical is methoxy-substituted phenyl radical.

32. The process of claim 1 further characterized in that 4H-3,1-benzoxazine-4-one is prepared by reacting about 1.0 mole of the isatoic anhydride with about 1.0 mole of the organic halide having the formula

wherein X is a halogen and R is a substituted or unsubstituted organic radical having up to 30 carbon atoms selected from the class consisting of alkyl, aryl, alkaryl, aralkyl, cycloalkyl and heterocyclic radicals.

33. The process of claim 32 further characterized in that X is chlorine.

34. The process of claim 32 further characterized in that R is an alkyl radical.

35. The process of claim 32 further characterized in that R is an aryl radical.

36. The process of claim 32 further characterized in that R is a styryl radical.

37. The process of claim 32 further characterized in that R is a phenyl radical.

38. The process of claim 32 further characterized in that R is a halo-substituted phenyl radical.

39. The process of claim 38 further characterized in that the halo-substituted phenyl radical is chlorophenyl.

40. The process of claim 32 further characterized in that R is an alkoxy-substituted phenyl radical.

41. The process of claim 40 further characterized in that the alkoxy-substituted phenyl radical is methoxyphenyl.

42. The process of claim 32 further characterized in that R is a nitro-substituted phenyl radical.

43. The process of claim 32 further characterized in that R is a halo-substituted alkyl radical.

44. The process of claim 43 further characterized in that the halo-substituted alkyl radical is chloromethyl.

45. The process of claim 32 further characterized in that R is furfuryl radical.

46. The process of claim 22 further characterized in that R is a furfuryl radical.

47. The process of claim 1 further characterized in that the substituted isatoic anhydride has the formula

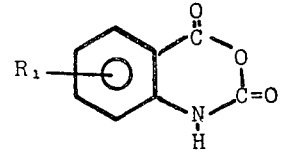

wherein $R_1$ is selected from the class consisting of hydrogen, halo, nitro, lower alkoxy, lower alkenyloxy and alkyl radical of 1 to 8 carbon atoms.

48. The process of claim 1 further characterized in that a 4H-3,1-benzoxazine-4-one is prepared by reacting about 1.0 mole of an isatoic anhydride with about 1.0 mole of an acyl halide having the formula

wherein X is chlorine.

49. The process of claim 1 further characterized in that a bis-4H-3,1-benzoxazine-4-one is prepared by reacting about 2.0 moles of an isatoic anhydride with 1.0 mole of an acyl halide having the formula

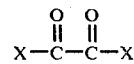

wherein X is chlorine.

50. The process of claim 1 further characterized in that a di-4H-3,1-benzoxazine-4-one is prepared by reacting about 2.0 moles of an isatoic anhydride with 1.0 mole of an acyl halide having the formula

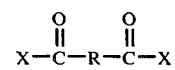

wherein X is chlorine.

* * * * *